US00PP09349P

United States Patent [19]

Lemon

[11] Patent Number: Plant 9,349

[45] Date of Patent: Oct. 31, 1995

[54] VARIETY OF GERANIUM NAMED ANGELA

[75] Inventor: David Lemon, Lompoc, Calif.

[73] Assignee: John Bodger & Sons Company, South El Monte, Calif.

[21] Appl. No.: 281,735

[22] Filed: Jul. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Fulwider, Patton, Lee & Utecht

[57] ABSTRACT

The cultivar is characterized by its dark clear pink color, Its compact, controlled growth habit and prolific blooms provide for superb cuttings and performs equally well in hanging baskets or in a ground bed. The blooms are very heat tolerant.

1 Drawing Sheet

BACKGROUND OF THE NEW PLANT

The present invention comprises a new and distinct cultivar of *Pelargonium* × *hortorum* known by the varietal name Angela (Oglevee No. 9045, Bodger No. 9GM 67-1). The new variety was discovered in a selective breeding program by David Lemon at Bodger Seeds, Ltd., Lompoc, Calif. The new variety is a selection from the crossing of Jackpot White × Bodger No. 8GM 262-2.

The new cultivar was first asexually reproduced by cuttings at Oglevee Ltd., Connellsville, Pa. It has been found to retain its distinctive characteristics through successive propagations.

The new cultivar, when grown in a glass greenhouse in Connellsville, Pa., using full light, 60° fahrenheit night temperature, 68° fahrenheit day temperature, 72° fahrenheit vent temperature and grown in a soilless media of constant fertilizer 200 to 250 parts per million of nitrogen and potassium has a response time of six weeks from the rooted cutting to a flowering plant in a 10.0 cm pot.

DESCRIPTION OF THE DRAWING

The company drawing illustrated a new cultivar, the color being as nearly true as possible with color illustrations of this type.

DESCRIPTION OF THE NEW PLANT

The following detailed description sets forth characteristics of the new cultivar. The data which defines each characteristics was collected from asexual reproductions carried out by Oglevee Ltd. in Connellsville, Pa. The plant histories were taken on rooted cuttings potted on Feb. 9, 1993 and flowered Mar. 23, 1993 under full light and greenhouse, and colorings were taken indoors under 200–220 foot candles of fluorescent cool white light using the R.H.S. Colour Chart of The Royal Horticultural Society of London.

THE PLANT

Classification:

*Botanical.*—*Pelargonium* × *hortorum.*

Form: Semi-dwarf, compact, lateral and cascading growth habit, free branching.

*Height.*—16.0–18.0 cm from the media surface.

*Growth.*—Lateral and procumbent habit; free basal branching.

*Strength.*—Free and early flowering; free standing; multipurpose uses.

Foliage: Light zone present, stalked leaf attachment.

Leaves:

*Size.*—7.0–9.0 cm across.

*Shape.*—Reniform; cordate base.

*Margin.*—Crenate.

*Texture.*—Pubescent.

*Color.*—Top: Leaf - Green Group 137C; Zone - Green Group 137A. Bottom: Yellow/green Group 146C.

*Ribs and veins.*—Palmate venation: Color: Yellow/Green group 147C.

Petioles:

*Length.*—6.5–9.0 cm.

*Color.*—Yellow/green group 146C.

Stem:

*Color.*—Yellow/green group 146D.

*Internodes.*—2.0–3.0 cm in length.

THE BUD

Shape: Upright; Hemispherical cluster.

Size: 1.5–2.0 cm across.

INFLORESCENCE

Blooming habit: Upright, continuous, very floriferous.

Size: 6.0–7.0 cm across.

Borne: floret on pedicel; pedicel on peduncle; 4.0–7.0 cm above foliage.

Florets:

*Form.*—Flat to slightly cupped.

*Color.*—Top: Red/purple group 62C; Bottom: Red/purple group 62D.

*Petals.*—12–14 in number; separate, not united; margin entire; obovate.

*Size.*—3.0–4.0 cm across.

*Texture and appearance.*—Smooth and satiny. Appearance from a distance is clean pink bloom with a small white eye above medium green foliage.

Petaloids:

*Quantity.*—0 to 5.

*Shape.*—Narrow, elongated, twisted.

*Color.*—Some White, others Red/purple group 62D.

Pedicel:

*Length.*—2.0–2.5 cm.

*Color.*—Yellow/green group 146C.

Peduncle: Arises from node opposite leaf petiole.

*Length.*—16.0–19.0 cm in length.

*Color.*—Yellow/green group 146B.

Persistence:

*Disease resistance.*—Not known.

*Lasting quality.*—Continuous blooming, very heat tolerant.

REPRODUCTIVE ORGANS

Stamens:

*Anthers.*—2.0–3.0 mm in length.

*Filaments.*—5.0–8.0 mm in length; white.

*Pollen.*—Golden Brown.

Pistils:

*Number.*—One.

*Length.*—5.0 mm.

*Stigma.*—One; 5–6 parted, pink in color.

*Style.*—2.0 mm, white to pale pink in color.

Ovaries: Superior, pubescent; pale green in color, 3.0–5.0 mm in length, 2.0 mm across.

Fruit: Occasional fruit noted.

GENERAL CHARATERISTICS

This new geranium variety, Angela, is an improvement on the current floribunda variety Grace. The flower color is a slightly darker clear pink color than Grace. The plant form is slightly larger yet very controlled in a neat mound habit.

For production purposes, Angela, is a very good cutting producer, is very heat tolerant and is a continuous bloomer. Angela can be used in either hanging baskets or ground beds.

I. claim:

1. A new and distinct variety of geranium plant, substantially as shown and described.

* * * * *

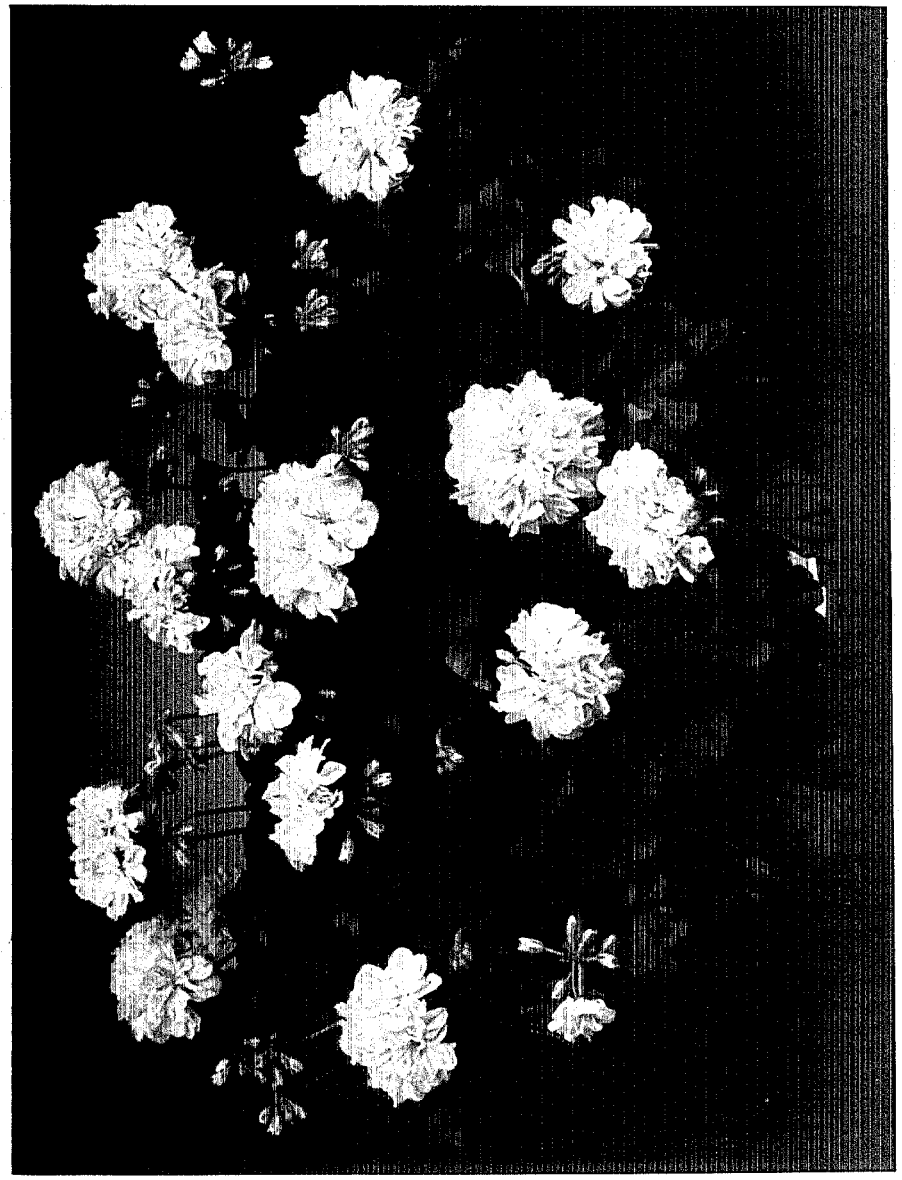

UNITED STATES PATENT AND TRADEMARK OFFICE

CERTIFICATE OF CORRECTION

PATENT NO. : Plant 9,349

DATED : October 31, 1995

INVENTOR(S) : David Lemon

It is certified that error appears in the above-identified patent and that said Letters Patent is hereby corrected as shown below:

Column 1, line 10, after "Pa." insert --,and has been repeatedly asexually reproduced by cuttings at Oglevee Ltd. in Connellsville, Pennsylvania.--

Column 1, line 21, delete "illustrated" and insert in its place --illustrates--

Signed and Sealed this

Fifth Day of March, 1996

*Attest:*

Bruce Lehman

BRUCE LEHMAN

*Attesting Officer*

*Commissioner of Patents and Trademarks*